(12) United States Patent
Burk et al.

(10) Patent No.: US 7,932,064 B2
(45) Date of Patent: Apr. 26, 2011

(54) PROCESSES FOR MAKING (R)-ETHYL 4-CYANO-3-HYDROXYBUTYRIC ACID

(75) Inventors: Mark J. Burk, San Diego, CA (US); Grace Desantis, San Diego, CA (US); Brian Morgan, San Diego, CA (US); Zoulin Zhu, San Diego, CA (US)

(73) Assignee: Verenium Corporation, San Diego, CA (US)

( * ) Notice: Subject to any disclaimer, the term of this patent is extended or adjusted under 35 U.S.C. 154(b) by 542 days.

(21) Appl. No.: 10/461,925

(22) Filed: Jun. 13, 2003

(65) Prior Publication Data

US 2004/0053378 A1 Mar. 18, 2004

Related U.S. Application Data

(60) Provisional application No. 60/389,317, filed on Jun. 13, 2002, provisional application No. 60/392,944, filed on Jun. 28, 2002.

(51) Int. Cl.
 *C12P 13/00* (2006.01)
 *C12N 9/78* (2006.01)
 *C07H 21/04* (2006.01)
 *C07H 21/02* (2006.01)

(52) U.S. Cl. ....... 435/128; 435/227; 536/23.1; 536/23.2

(58) Field of Classification Search .................. 435/128, 435/183, 6, 69.1, 146, 320.1, 325; 536/23.2
See application file for complete search history.

(56) References Cited

U.S. PATENT DOCUMENTS

| | | | |
|---|---|---|---|
| 4,611,067 A | 9/1986 | Volante | |
| 5,003,080 A | 3/1991 | Butler | |
| 5,097,045 A | 3/1992 | Butler | |
| 5,103,024 A | 4/1992 | Millar | |
| 5,124,482 A | 6/1992 | Butler | |
| 5,149,837 A | 9/1992 | Butler | |
| 5,216,174 A | 6/1993 | Butler | |
| 5,245,047 A | 9/1993 | Butler | |
| 5,248,793 A | 9/1993 | Millar | |
| 5,280,126 A | 1/1994 | Butler | |
| 5,298,627 A | 3/1994 | Butler | |
| 5,342,952 A | 8/1994 | Butler | |
| 5,397,792 A | 3/1995 | Butler | |
| 5,446,054 A | 8/1995 | Butler | |
| 5,470,981 A | 11/1995 | Butler | |
| 5,489,690 A | 2/1996 | Butler | |
| 5,489,691 A | 2/1996 | Butler | |
| 5,510,488 A | 4/1996 | Butler | |
| 5,629,190 A | 5/1997 | Petre | |
| 5,635,391 A | 6/1997 | Petre | |
| 5,872,000 A | 2/1999 | Yu | |
| 5,939,553 A * | 8/1999 | Reichwein et al. | 546/250 |
| 6,433,213 B1 | 8/2002 | Bosch | |
| 6,596,879 B2 | 7/2003 | Bosch | |
| 2003/0044800 A1 | 3/2003 | Connelly | |
| 2004/0014195 A1 * | 1/2004 | DeSantis et al. | 435/228 |

FOREIGN PATENT DOCUMENTS

| | | |
|---|---|---|
| EP | 0 178 106 | 3/1993 |
| WO | 01/48175 A2 | 7/2001 |
| WO | 02/29079 A2 | 4/2002 |
| WO | 03/000840 A2 | 1/2003 |
| WO | WO-03/004456 | 1/2003 |
| WO | WO 03/097810 | 11/2003 |
| WO | 2004/096988 A2 | 11/2004 |

OTHER PUBLICATIONS

Effenberger et al. Selective hydrolysis of aliphatic dinitriles to monocarboxylic acids by a nitrilase from *Arabidopsis thaliana*, Synthesis 2001, 11866-1872.*
Gradley et al. Biotechnol Letters, 16(1): 41-46, 1994.*
International Search Report mailed on May 12, 2004, for PCT patent application No. PCT/US03/18840, filed on Jun. 13, 2002, 3 pages.
Baumann et al., Tetrahedron Letters (1992) 33:2283-2284.
Brower et al., Tetrahedron Letters (1992) 33:2279-2282.
Cohen et al., Tetrahedron Letters (1990) 31:7223-7226.
Gavagan et al., J. Org. Chem. (1998) 63:4792-4801.
Kobayashi et al., Tetrahedron (1990) 46:5587-5590.
Robertson—Applied and Environmental Microbiology (2004)—70—2429-2436.
EP08731180—Extended European Search Report—Jul. 2, 2010.
EP03753097—Office Action—Aug. 11, 2010.
EP03753097—Supplementary Partial EP Search Report—Sep. 21, 2007.

\* cited by examiner

*Primary Examiner* — Anand U Desai
*Assistant Examiner* — Iqbal H Chowdhury (57) ABSTRACT

The invention provides novel processes for making ethyl-4-cyano-3-hydroxybutyrate, e.g., (R)-ethyl 4-cyano-3-hydroxybutyric acid, and 4-cyano-3-hydroxybutyric acid. The invention provides protocols for making and 4-cyano-3-hydroxybutyric acid and ethyl-4-cyano-3-hydroxybutyrate by whole cell processes, cell lysate processes, "one pot processes" and "multi-pot" processes using a variety of parameters.

32 Claims, 1 Drawing Sheet

FIGURE 1

PROCESSES FOR MAKING (R)-ETHYL 4-CYANO-3-HYDROXYBUTYRIC ACID

CROSS-REFERENCES TO RELATED APPLICATIONS

This application claims the benefit of priority under 35 U.S.C. §119(e) of U.S. Provisional patent application Ser. No. (U.S. Ser. No.) 60/389,317, filed Jun. 13, 2002, and U.S. Ser. No. 60/392,944, filed Jun. 28, 2002. These applications are hereby incorporated by reference into the subject application in their entireties for all purposes.

TECHNICAL FIELD

This invention relates to synthetic chemistry. In alternative aspects, the invention provides novel processes for making an ethyl-4-cyano-3-hydroxybutyrate, e.g., (R)-ethyl-4-cyano-3-hydroxybutyrate, and a 4-cyano-3-hydroxybutyric acid. The invention provides protocols for making and 4-cyano-3-hydroxybutyric acid and ethyl-4-cyano-3-hydroxybutyrate by whole cell processes, cell lysate processes, "one pot processes" and "multi-pot" processes using a variety of parameters.

BACKGROUND

Atorvastatin, e.g., LIPITOR™, is used as a selective and competitive inhibitor of the enzyme 3-hydroxy-3-methylglutaryl-coenzyme A (HMG-CoA) reductase, the rate-limiting enzyme that converts 3-hydroxy-3-methylglutaryl-coenzyme A to mevalonate, a precursor of sterols such as cholesterol. The conversion of HMG-CoA to mevalonate is an early and rate-limiting step in cholesterol biosynthesis. Atorvastatin is indicated, in conjunction with dietary restriction, in the management of hyperlipidemia, including hypercholesterolemia, mixed dyslipidemia, and homozygous familial hypercholesterolemia.

(R)-ethyl 4-cyano-3-hydroxybutyrate is a key intermediate in the synthesis of atorvastatin.

Crosby, John A.; Parratt, Julian S.; Turner, Nicholas J., Dep. Chem., Univ. Exeter, Exeter, UK. Tetrahedron: Asymmetry (1992), 3(12), 1547-1550, reported enzymatic hydrolysis of prochiral dinitriles, where a series of prochiral 3-hydroxyglutaronitrile derivatives were enzymatically hydrolyzed to corresponding nitrile-carboxylic acids with enantiomeric excesses of 22% to 84%. The products were of the (S)-configuration in all cases.

Effenberger, Franz; Osswald, Steffen., Institut fur Organische Chemie, Universitat Stuttgart, Stuttgart, Germany. Synthesis (2001), (12), 1866-1872, reported selective hydrolysis of aliphatic dinitriles to monocarboxylic acids by a nitrilase from *Arabidopsis thaliana* expressed in *E. coli*. Conversion rate and selectivity of the hydrolysis of dinitriles w-cyanocarboxylic acids depended on the chain length.

SUMMARY

The invention provides a novel process for a key intermediate to atorvastatin (e.g., LIPITOR™), or (R)-ethyl 4-cyano-3-hydroxybutyrate ((R)-ethyl 4-cyano-3-hydroxybutyric acid). In one aspect, the process of the invention uses epichlorohydrin as starting material and yields the target product (R)-ethyl 4-cyano-3-hydroxybutyric acid (i.e., (R)-ethyl 4-cyano-3-hydroxybutyrate). In one aspect, the processes of the invention yield a product with a chiral purity of more than 99% ee.

The invention provides protocols for making (R)-ethyl-4-cyano-3-hydroxybutyrate by both "one pot processes" and "multi-pot" processes using a variety of parameters, as described herein.

The invention provides methods for making 4-cyano-3-hydroxybutyric acid comprising the following steps: (a) providing a 3-hydroxyglutaronitrile, or equivalent; (b) providing a polypeptide having a nitrilase activity; and (c) catalyzing the conversion of the 3-hydroxyglutaronitrile, or equivalent to 4-cyano-3-hydroxybutyric acid by contacting the 3-hydroxyglutaronitrile, or equivalent, with the polypeptide having a nitrilase activity.

The invention provides methods for making 4-cyano-3-hydroxybutyric acid comprising the following steps (a) providing an epichlorohydrin, or equivalent; (b) providing a polypeptide having a nitrilase activity; (c) converting the epichlorohydrin to 3-hydroxyglutaronitrile; and (d) catalyzing the conversion of the 3-hydroxyglutaronitrile to 4-cyano-3-hydroxybutyric acid by contacting the 3-hydroxyglutaronitrile with the polypeptide having a nitrilase activity.

The invention provides methods for making ethyl-4-cyano-3-hydroxybutyric acid comprising the following steps (a) providing a 3-hydroxyglutaronitrile, or equivalent; (b) providing a polypeptide having a nitrilase activity; (c) catalyzing the conversion of the 3-hydroxyglutaronitrile, or equivalent to 4-cyano-3-hydroxybutyric acid by contacting the 3-hydroxyglutaronitrile, or equivalent, with the polypeptide having a nitrilase activity; and (d) converting the 4-cyano-3-hydroxybutyric acid to ethyl-4-cyano-3-hydroxybutyric acid.

The invention provides methods for making atorvastatin comprising the following steps (a) providing a 3-hydroxyglutaronitrile, or equivalent; (b) providing a polypeptide having a nitrilase activity; (c) catalyzing the conversion of the 3-hydroxyglutaronitrile, or equivalent to 4-cyano-3-hydroxybutyric acid by contacting the 3-hydroxyglutaronitrile, or equivalent, with the polypeptide having a nitrilase activity; (d) converting the 4-cyano-3-hydroxybutyric acid to ethyl-4-cyano-3-hydroxybutyric acid; and (e) converting the ethyl-4-cyano-3-hydroxybutyric acid to atorvastatin.

In one aspect, the epichlorohydrin is converted to 3-hydroxyglutaronitrile by cyanide treatment.

In one aspect, the polypeptide having a nitrilase activity is a nitrilase, or, a catalytic antibody. In one aspect, the polypeptide having a nitrilase activity is a peptidomimetic.

In one aspect, the polypeptide having a nitrilase activity is affixed to a solid support, e.g., glass, ceramic, quartz, Sepharose, gelatin, glutaraldehyde, chitosan-treated glutaraldehyde, albumin-glutaraldehyde, chitosan-Xanthan, toyopearl gel (polymer gel), alginate, alginate-polylysine, carrageenan, agarose, glyoxyl agarose, magnetic agarose, dextran-agarose, poly(Carbamoyl Sulfonate) hydrogel, BSA-PEG hydrogel, phosphorylated polyvinyl alcohol (PVA), monoaminoethyl-N-aminoethyl (MANA), amino, or any combination thereof.

In one aspect, the methods further comprise isolating the 4-cyano-3-hydroxybutyric acid by precipitation with calcium hydroxide. In one aspect, the methods further comprise a step of isolating the 4-cyano-3-hydroxybutyric acid by distillation, column chromatography, crystallization or precipitation. In one aspect, the precipitation step comprises a $Ca^{2+}$ salt precipitation, e.g., where the calcium salt comprises $CaCl_2$. In one aspect, the crystallization step comprises use of a potassium salt, a sodium salt, a lithium salt, a rubidium salt, a cesium salt, a monovalent salt or a divalent metal salt.

In one aspect, the methods further comprise one or more steps of recrystallizing the 4-cyano-3-hydroxybutyric acid. In one aspect, the iterative recrystallizing results in product with progressively higher degrees of enantiospecificity, e.g., 95% ee, 99% ee, 99.5% ee or higher. In one aspect, the recrystallization step comprises use of a sodium salt, a lithium salt, a rubidium salt, a cesium salt, a monovalent salt or a divalent metal salt.

In one aspect, the methods further comprise conversion of the 4-cyano-3-hydroxybutyric acid to ethyl-4-cyano-3-hydroxybutyric acid. In one aspect, the methods further comprise conversion of the 4-cyano-3-hydroxybutyric acid to ethyl-4-cyano-3-hydroxybutyric acid by esterification. In one aspect, the esterification comprises a Fisher esterification reaction, a transesterification reaction or an esterification under Mitsunobu conditions.

In one aspect, a product of a method of the invention is an (R)-enantiomer, or, an (S)-enantiomer, e.g., in one aspect the ethyl 4-cyano-3-hydroxybutyric acid is an (R)-ethyl 4-cyano-3-hydroxybutyric acid or an (S)-ethyl 4-cyano-3-hydroxybutyric acid.

In one aspect, the (R)-ethyl 4-cyano-3-hydroxybutyric acid product has an enantiomeric purity of between about 80% ee to 99.5% ee, between about 90% ee to 99% ee, or 99% ee, 99.5% ee or higher.

In one aspect, the reaction is a one-pot reaction, or, at least two steps of the reaction take place in sequential pots (a "pot" can be any container or equivalent, e.g., a whole cell, such as a bacterial or a mammalian cell). In one aspect, at least one step of the reaction takes place in a whole cell. The cell can be encapsulated, e.g., in a gel. In one aspect, at least one step of the reaction takes place in a whole cell in a fermentor. In one aspect, at least one step of the reaction takes place in a cell lysate or a whole cell paste. In one aspect, at least one step of the reaction takes place in a membrane reactor, a capillary, or a column. The capillary can comprise a capillary array, e.g., a GIGAMATRIX™.

In one aspect, the methods further comprise converting the 4-cyano-3-hydroxybutyric acid to its potassium salt by reaction with a potassium hydroxide in water, methanol or ethanol. In one aspect, the methods further comprise crystallization of the 4-cyano-3-hydroxybutyric acid potassium salt.

In one aspect, the preparation of hydroxyglutaronitrile from epichlorohydrin is followed by the addition of a neutralizing agent, a buffer or a diluent, and then subsequent conversion to 4-cyano-3-hydroxybutyric acid with the nitrilase. The preparation of hydroxyglutaronitrile from epichlorohydrin, the addition of a neutralizing agent, a buffer or a diluent, and the conversion to 4-cyano-3-hydroxybutyric acid with the nitrilase can take place in a single pot (container), or each step can be in a different pot (container), or, a combination thereof.

In one aspect, at least one step of the reaction takes place under conditions comprising a temperature in a range between about 4° C. and about 80° C., a range between about 10° C. and about 40° C., or a range between about 22° C. and 37° C.

In one aspect, at least one step of the reaction takes place under conditions comprising a pH in a range between about pH 4 and about pH 11, or, in a range between about pH 5 and about pH 9.

In one aspect, substrate concentrations are in the range of between about 5 M, or higher, to 10 mM, or lower.

In one aspect, the nitrilase used in a method of the invention is an isolated or recombinant polypeptide having a sequence at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%,83%, 84%, 85%, 86%, 87%, 88%, 89%, 90%, 91%, 92%, 93%, 94%, 95%, 96%, 97%, 98%, 99%, or more, or complete sequence identity to SEQ ID NO:2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 378, 380, 382, 384, 386, or enzymatically active subsequences thereof.

In one aspect, the nitrilase comprises a sequence as set forth in SEQ ID NO:196, SEQ ID NO:206, SEQ ID NO:208, SEQ ID NO:210 or SEQ ID NO:238 and having one or more mutations selected from the group consisting of a mutation at residue 55 lysine, residue 55 glycine, residue 55 glutamine, residue 60 glutamic acid, residue 111 serine, residue 190, residue 190 serine, residue 190 histidine, residue 190 tyrosine, residue 190 threonine, residue 191 leucine, residue 191 valine, residue 191 methionine, residue 191 aspartic acid, residue 191 glycine, residue 191 glutamic acid, residue 191 tyrosine, residue 191 threonine, residue 199 glutamic acid, residue 199 leucine, residue 222 leucine, and any combination thereof.

In one aspect, the nitrilase comprises a sequence as set forth in SEQ ID NO:196, SEQ ID NO:206, SEQ ID NO:208, SEQ ID NO:210 or SEQ ID NO:238 and having a mutation at residue 190 or equivalent, wherein alanine is replaced with a hydrogen-binding amino acid or hydrogen-binding peptidomimetic residue.

In one aspect, the nitrilase comprises a sequence as set forth in SEQ ID NO:196, SEQ ID NO:206, SEQ ID NO:208, SEQ ID NO:210 or SEQ ID NO:238 and having a mutation at residue 190 or equivalent, wherein alanine is replaced with a hydrophobic amino acid or hydrophobic peptidomimetic residue.

In one aspect, the nitrilase comprises a sequence having the equivalent of one or more mutations at residue 55 lysine, glycine, or glutamine; at residue 60 glutamic acid; at residue 111 serine, at residue 190, serine, histidine, tyrosine or threonine; at residue 191, leucine, valine, methionine, aspartic acid, glycine, glutamic acid, tyrosine or threonine; at residue 199 glutamic acid or leucine; at residue 222 leucine of SEQ ID NO:196, SEQ ID NO:206, SEQ ID NO:208, SEQ ID NO:210 or SEQ ID NO:238.

In one aspect, the nitrilase is encoded by a nucleic acid having a sequence at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%,76%, 77%, 78%, 79%, 80%, 81%, 82%, 83%, 84%, 85%, 86%, 87%, 88%, 89%, 90%,91%, 92%, 93%, 94%, 95%, 96%, 97%, 98%, 99%, or more, or complete sequence identity to SEQ ID NO:1, 3, 5, 7, 9, 11, 13, 15, 17, 19, 21, 23, 25, 27, 29, 31, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 377, 379, 381, 383 or 385.

The details of one or more embodiments of the invention are set forth in the accompanying drawings and the description below. Other features, objects, and advantages of the invention will be apparent from the description and drawings, and from the claims.

All publications, patents, patent applications, GenBank sequences and ATCC deposits, cited herein are hereby expressly incorporated by reference for all purposes.

DESCRIPTION OF DRAWINGS

Like reference symbols in the various drawings indicate like elements.

DETAILED DESCRIPTION

Figure 1:
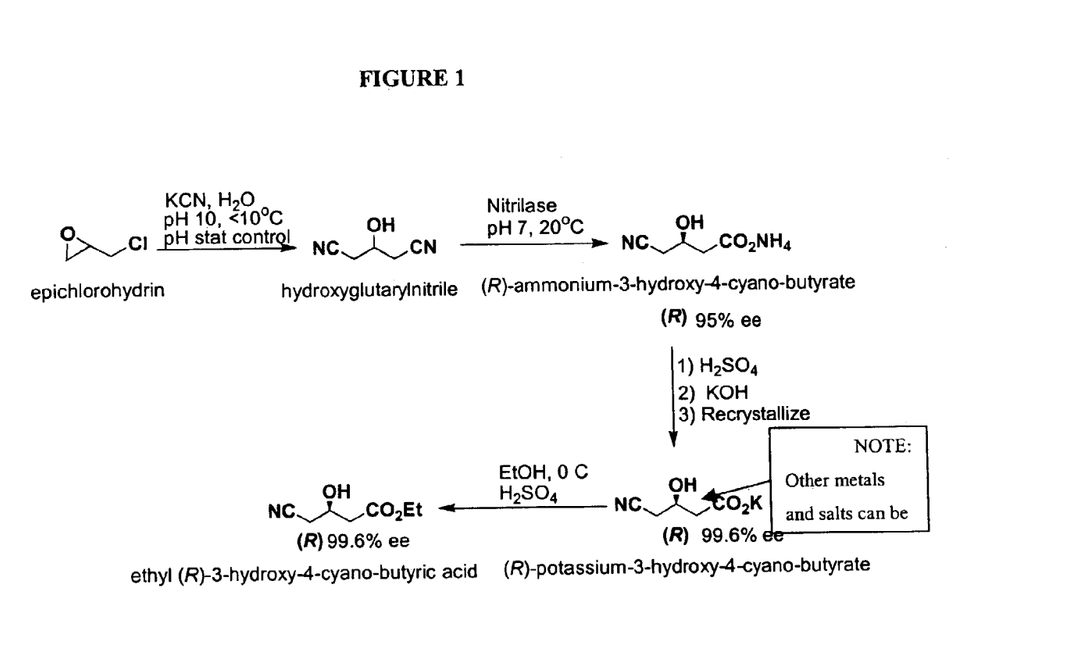
FIG. 1 schematically illustrates an exemplary method of the invention using epichlorohydrin to yield the product (R)-ethyl 4-cyano-3-hydroxybutyric acid.

The methods of the invention use epichlorohydrin, or equivalent, as a starting material to yield the product (R)-ethyl-4-cyano-3-hydroxybutyrate. In one aspect, the product is produced with a chiral purity of more than 99% ee.

In one aspect of the processes of the invention, epichlorohydrin is converted to 3-hydroxyglutaronitrile (HGN) by cyanide treatment under pH and temperature control, with high yield and purity. In one aspect of the processes of the invention, 3-hydroxyglutaronitrile (HGN), whether prepared by this method or another process, whether a crude product (e.g., without isolation) or an isolated pure composition, is converted to 4-cyano-3-hydroxybutyric acid by catalysis with a nitrilase. Any nitrilase can be used.

In one aspect, the processes of the invention produce an enantiomerically pure product, e.g., an (R)-ethyl-4-cyano-3-hydroxybutyrate. In alternative aspects of the process, the product is 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.9% or 100% enantiomerically pure, for example the processes of the invention yielding a product having an enantiomeric excess of between about 85% ee to about 99.5% ee. In one aspect, the chiral product is an (R)-enantiomer. In another aspect, the chiral product is an (S)-enantiomer.

In one aspect, the processes of the invention yield a product having an enantiomeric excess of between about 90% ee to 99% ee. It was demonstrated that this acid product (4-cyano-3-hydroxybutyric acid) can be isolated via precipitation with calcium hydroxide. The precipitate can then be converted into (R)-ethyl-4-cyano-3-hydroxybutyrate by esterification, in a one-pot reaction.

In another aspect, the acid product can be converted to its potassium salt by reaction with potassium hydroxide in water, methanol or ethanol. A process is established whereby crystallization of this potassium salt from ethanol or methanol/MTBE is shown to upgrade the enantiomeric excess of the acid to greater than 99% ee. In one aspect, the process is carried out with and/or without the crystallization step or with and without a $Ca^{2+}$ salt precipitation step.

In another aspect, the methods include the sequential preparation of hydroxyglutaronitrile (HGN) from epichlorohydrin followed by the addition of neutralizing agent, buffer or other diluents and then subsequent transformation with a nitrilase or the direct addition of a nitrilase to the crude reaction of the HGN production.

In another aspect, a 4-cyano-3-hydroxy butyrate ester may be made (in another aspect, in the same pot) through a variety of methods (see below).

In another aspect, sequential pots are used for two or more or all or the different steps of the reaction. In one aspect, crude preparations, or purified materials, or both, are transferred to new vessels.

In one aspect, the nitrilase reaction is applied to purify crude hydroxyglutaronitrile (HGN). In alternative aspects, purification can be by distillation, column chromatography, crystallization (e.g. K+ salt) or precipitation (e.g. $CaCl_2$).

In alternative aspects, various types of crystallizing salts (not only potassium) can be used. Other types of crystallizing salts can be used include sodium, lithium, rubidium, cesium or any other monovalent or divalent metal.

The invention provides several ways of doing esterification, including Fisher esterification (e.g., Fisher-Speier esterification, see, e.g., Srinivas (1990) J. Chromatogr. 530: 327-336), catalyzed by HCl, sulfuric acid, or other acids including acidic resins; or, esterification under Mitsunobu conditions (see, e.g., Ahn (2002) J. Org. Chem. 67:1751-1753; Ahn (2002) J. Org. Chem. 67:1754-1759). The methods of the invention can be practiced with any protocol for the preparation of esters, including under preparation of esters Mitsunobu conditions or any other method known in the art, including transesterification. In alternative aspects, the methods of the invention can be practiced with other esters if possible: methyl, ethyl, propyl, iso-propyl, butyl etc.

In alternative aspects, the invention provides various preparations of tert-butyl esters by treatment of the salt with tert-butyl bromide and the preparation of esters by treatment of carboxylic acid with dehydrating agents (e.g. DCC-dicyclohexylcarbodimide) and an alcohol.

In alternative aspects, processes of the invention can be performed directly in a fermentor with whole cells, with whole cell paste (e.g., wet or dry, immobilized or free), using cell lysates, e.g., crude, semi-processed, unprocessed or clarified lysate, lyophilized or not, or immobilized or free lysate preparations.

The methods of the invention can be practiced with purified or partially purified nitrilase. The nitrilase can be encapsulated within a gel. If whole cells are used, they can be encapsulated within a gel.

In alternative aspects, the processes of the invention can be run in a batch wise process or via pulsed or continuous feeding of substrate in a number of reactor configurations, including a membrane reactor or column.

In alternative aspects, the processes of the invention can be run using temperatures in the range of 2° C., 4° C., 10° C., 15° C., 22° C., 30° C., 37° C., 40° C. (e.g., in a range of between about 4° to about 40° C.), 45° C., 50° C., 55° C., 60° C., 65° C., 75° C., to protect as high as 80° C. or more. The processes of the invention can be run using pH in the range of about 5 to about 9, or, from about pH 4 to about pH 11, at a pH of about 2, 3, 4, 5, 6, 7, 8, 9, 10, 11, 12 or higher, or lower.

In alternative aspects, the processes of the invention can be run using substrate concentrations as high at 5 M and as low as 10 mM, e.g., at a substrate concentration of about 5 mM, 10 mM, 20 mM, 50 mM, 100 mM, 150 mM, 200 mM, 250 mM, 300 mM, 350 mM, 400 mM, 450 mM, 500 mM, 550 mM, 600 mM, 700 mM, 800 mM, 900 mM, 1 M, 1.5 M, 2 M, 2.5 M, 4 M, 3.5 M, 4 M, 4.5 M 5 M, or higher, or lower.

In alternative aspects, the processes of the invention can be run using various ionic strengths and buffer conditions. The process of the invention can be run using no buffer under pH stat conditions or in saline unbuffered.

General Methods

In various aspects, the invention provides processes for making 4-cyano-3-hydroxybutyric acid and ethyl-4-cyano-3-hydroxybutyrate. The invention can be practiced in conjunction with any method or protocol known in the art, which are well described in the scientific and patent literature.

The skilled artisan will recognize that the starting and intermediate compounds used in the methods of the invention can be synthesized using a variety of procedures and methodologies, which are well described in the scientific and patent literature., e.g., Organic Syntheses Collective Volumes, Gilman et al. (Eds) John Wiley & Sons, Inc., NY; Venuti (1989) Pharm Res. 6:867-873. The invention can be practiced in conjunction with any method or protocol known in the art, which are well described in the scientific and patent literature. Enzymes of the invention, and the enzymes used in the methods of the invention, can be produced by any synthetic or recombinant method, or, they may be isolated from a natural source, or, a combination thereof.

The compositions used to practice the invention, including nucleic acids and proteins used to practice the methods of the invention can be detected, confirmed and quantified by any of a number of means well known to those of skill in the art. General methods for detecting reaction products of the methods of the invention, starting products and intermediates, nucleic acids and proteins used to practice the invention, and the like, include analytic biochemical methods such as spectrophotometry, radiography, electrophoresis, capillary electrophoresis, high performance liquid chromatography (HPLC),thin layer chromatography (TLC), hyperdiffusion chromatography, and the like, and various immunological methods such as fluid or gel precipitin reactions, immunodiffusion (single or double), immunoelectrophoresis, radioimmunoassays (RIAs), enzyme-linked immunosorbent assays (ELISAs), immunofluorescent assays, and the like. The detection of nucleic acids can be by well known methods such as Southern analysis, northern analysis, gel electrophoresis, PCR, radiolabeling, scintillation counting, and affinity chromatography.

The discussion of the general methods given herein is intended for illustrative purposes only. Other alternative methods and embodiments will be apparent to those of skill in the art upon review of this disclosure.

Nitrilases

In one aspect of the processes of the invention, 3-hydroxyglutaronitrile (HGN) is transformed into 4-cyano-3-hydroxybutyric acid catalyzed by a nitrilase. Any nitrilase can be used to practice the invention. Nitrilases are capable of converting nitrites directly to carboxylic acids. Nitrilase enzymes used to practice the methods of the invention are found in a wide range of mesophilic micro-organisms, including species of *Bacillus, Norcardia, Bacteridium, Rhodococcus, Micrococcus, Brevibacterium, Alcaligenes, Acinetobacter, Corynebacterium, Fusarium* and *Klebsiella*. Additionally, nitrilase enzymes used to practice the methods of the invention include isolated and recombinant thermophilic nitrilases, some of which can be derived from bacteria.

In one aspect, a nitrilase used in a method of the invention is an isolated or recombinant polypeptide encoded by a nucleic acid having at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%,81%, 82%, 83%, 84%, 85%, 86%, 87%, 88%, 89%, 90%, 91%, 92%, 93%, 94%, 95%, 96%, 97%, 98%, 99%, or more, or complete sequence identity (100% identical) to SEQ ID NO:1, 3, 5, 7, 9, 11, 13, 15, 17, 19, 21, 23, 25, 27, 29, 31, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 377, 379, 381, 383, 385, or variants or subsequences thereof.

In one aspect, a nitrilase used in a method of the invention is an isolated or recombinant polypeptide having a sequence at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete sequence identity (100% identical) to SEQ ID NO:2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 378, 380, 382, 384, 386, or variants thereof, or active subsequences thereof.

Exemplary nitrilase variants that can be used in the methods of the invention may include, for example, the following variations of SEQ ID NO:195, 205, 207, 209, or 237, having one or more mutations: at positions 163-165 AAA, AAG, GGT, GGC, GGA, GGG, CAA, or CAG; at positions 178-180 GAA or GAG; at positions 331-333 TCT, TCC, TCA, TCG, AGT, or AGC; at positions 568-570 CAT, CAC, TCT, TCC, TCA, TCG, AGT, AGC, ACT, ACC, ACA, TCA, TAT, TAC, ATG or ACG; at positions 571-573 TTA, TTG, CTT, CTC, CTA, CTG, GTT, GTC, GTA, GTG, ATG, ACT, ACC, ACA, GAT, GAC, GGT, GGC, GGA, GGG, GAA, GAG, TAT, TAC, or ACG; at positions 595-597 GAA, GAG, TTA, TTG, CTT, CTC, CTA, or CTG; at positions 664-666 TTA, TTG, CTT, CTC, CTA, or CTG; or any combination thereof.

Exemplary nitrilase variants that can be used in the methods of the invention may also include the following variations of SEQ ID NO:196, 206, 208, 210 or 238, having one or more mutations: at residue 55 lysine, glycine, or glutamine; at residue 60 glutamic acid; at residue 111 serine, at residue 190, serine, histidine, tyrosine or threonine; at residue 191, leucine, valine, methionine, aspartic acid, glycine, glutamic acid, tyrosine or threonine; at residue 199 glutamic acid or leucine; at residue 222 leucine; or any combination thereof.

Exemplary nitrilases that can be used in the methods of the invention may also include fragments of an enzyme, e.g., as described herein. In one aspect, the nitrilase used in the methods of the invention can be at least 20, 20, 40, 50, 60, 70, 80, 90 or 100 or more amino acids in length. Exemplary nitrilases that can be used in the methods of the invention may also include peptidomimetics having nitrilase activity. The nitrilases that can be used in the methods of the invention can be codon-optimized polypeptides or fragments thereof, wherein the codon usage is optimized for a particular organism or cell or lysate.

In one aspect of the invention, the invention uses nitrilase variants having improved or diminished enantioselectivity, for example, in the conversion of a 3-hydroxyglutarylnitrile (HGN) to (R)-4-cyano-3-hydroxybutyrate, than one of the exemplary polypeptides noted herein.

Immobilized Polypeptide Solid Supports

The polypeptides having a nitrilase activity, e.g., enzymes, catalytic antibodies and fragments thereof, can be affixed to a solid support. In one aspect, a mixture of enzymes or active fragments thereof used for various steps in a process of the invention are attached to a solid support. In one aspect, they can be immersed into a reaction pot, a lysate, a process vat, and the like. The solid support can be taken out of the pot, vat, etc. along with the enzymes affixed thereto, for repeated use. In one aspect of the invention, the solid support is a capillary, a gel, a resin, a polymer, a ceramic, a glass, a quartz, a microelectrode and any combination thereof. High throughput apparatus can be adapted and used to practice the methods of the invention, see, e.g., U.S. patent application No. 20020001809.

For example, solid supports useful in the methods of the invention include gels. Some examples of gels include Sepharose, gelatin, glutaraldehyde, chitosan-treated glutaraldehyde, albumin-glutaraldehyde, chitosan-Xanthan, toyopearl gel (polymer gel), alginate, alginate-polylysine, carrageenan, agarose, glyoxyl agarose, magnetic agarose, dextran-agarose, poly(Carbamoyl Sulfonate)hydrogel, BSA-PEG hydrogel, phosphorylated polyvinyl alcohol (PVA), monoaminoethyl-N-aminoethyl (MANA), amino, or any combination thereof.

Another solid support useful in the present invention are resins or polymers. Some examples of resins or polymers include cellulose, acrylamide, nylon, rayon, polyester, anion-exchange resin, AMBERLITE™ XAD-7, AMBERLITE™ XAD-8, AMBERLITE™ IRA-94, AMBERLITE™ IRC-50, polyvinyl, polyacrylic, polymethacrylate, or any combination thereof.

Another type of solid support useful in the present invention is ceramic. Some examples include non-porous ceramic, porous ceramic, $SiO_2$, $Al_2O_3$. Another type of solid support useful in the present invention is glass. Some examples include non-porous glass, porous glass, aminopropyl glass or any combination thereof. Another type of solid support that can be used is a microelectrode. An example is a polyethyleneimine-coated magnetite. Graphitic particles can be used as a solid support. Another example of a solid support is a cell, such as a red blood cell.

Methods of Immobilization

There are many methods that would be known to one of skill in the art for immobilizing antibodies, enzymes or fragments thereof, or reagents or catalysts, onto a solid support. Some examples of such methods include, e.g., electrostatic droplet generation, electrochemical means, via adsorption, via covalent binding, via cross-linking, via a chemical reaction or process, via encapsulation, via entrapment, via calcium alginate, or via poly(2-hydroxyethyl methacrylate). Like methods are described in Methods in Enzymology, Immobilized Enzymes and Cells, Part C. 1987. Academic Press. Edited by S. P. Colowick and N. O. Kaplan. Volume 136; and Immobilization of Enzymes and Cells. 1997. Humana Press. Ed. G. F. Bickerstaff. Series: Methods in Biotechnology, Ed. J. M. Walker.

Arrays

Reagents, catalysts and polypeptides (e.g., nitrilases) and the like used to practice the invention can be immobilized by application to an array. Capillary arrays, such as the GIGAMATRIX™, Diversa Corporation, San Diego, Calif.; and arrays described in, e.g., U.S. patent application No. 20020080350 A1; WO 0231203 A; WO 0244336 A, provide an alternative apparatus for practicing the invention.

In practicing the methods of the invention, any known array and/or method of making and using arrays can be incorporated in whole or in part, or variations thereof, as described, for example, in U.S. Pat. Nos. 6,277,628; 6,277,489; 6,261,776; 6,258,606; 6,054,270; 6,048,695; 6,045,996; 6,022,963; 6,013,440; 5,965,452; 5,959,098; 5,856,174; 5,830,645; 5,770,456; 5,632,957; 5,556,752; 5,143,854; 5,807,522; 5,800,992; 5,744,305; 5,700,637; 5,556,752; 5,434,049; see also, e.g., WO 99/51773; WO 99/09217; WO 97/46313; WO 96/17958; see also, e.g., Johnston (1998) Curr. Biol. 8:R171-R174; Schummer (1997) Biotechniques 23:1087-1092; Kern (1997) Biotechniques 23:120-124; Solinas-Toldo (1997) Genes, Chromosomes & Cancer 20:399-407; Bowtell (1999) Nature Genetics Supp. 21:25-32. See also published U.S. patent application Nos. 20010018642; 20010019827; 20010016322; 20010014449; 20010014448; 20010012537; 20010008765.

Antibodies and Antibody-Based Screening Methods

Isolated or recombinant antibodies are used to practice the invention, e.g., catalytic antibodies having a nitrilase activity can be used in the processes of the invention. Alternatively, antibodies can be used to isolate, identify or quantify the nitrilases or related polypeptides used to practice the methods of the invention.

Methods of immunization, producing and isolating antibodies (polyclonal and monoclonal) are known to those of skill in the art and described in the scientific and patent literature, see, e.g., Coligan, CURRENT PROTOCOLS IN IMMUNOLOGY, Wiley/Greene, N.Y. (1991); Stites (eds.) BASIC AND CLINICAL IMMUNOLOGY (7th ed.) Lange Medical Publications, Los Altos, Calif.; Goding, MONOCLONAL ANTIBODIES: PRINCIPLES AND PRACTICE (2d ed.) Academic Press, New York, N.Y. (1986); Kohler (1975) Nature 256:495; Harlow (1988) ANTIBODIES, A LABORATORY MANUAL, Cold Spring Harbor Publications, New York. Antibodies also can be generated in vitro, e.g., using recombinant antibody binding site expressing phage display libraries, in addition to the traditional in vivo methods using animals. See, e.g., Hoogenboom (1997) Trends Biotechnol. 15:62-70; Katz (1997) Annu. Rev. Biophys. Biomol. Struct. 26:27-45.

Whole Cell Engineering and Measuring Metabolic Parameters

The methods of the invention can be practiced in whole or in part in a whole cell environment. The invention also provides for whole cell evolution, or whole cell engineering, of a cell to develop a new cell strain having a new phenotype to be used in the methods of the invention, e.g., a new cell line comprising one, several or all enzymes needed to practice a method of the invention. This can be done by modifying the genetic composition of the cell, where the genetic composition is modified by addition to the cell of a nucleic acid, e.g., a coding sequence for an enzyme used in the methods of the invention. See, e.g., WO0229032; WO0196551.

The host cell for the "whole-cell process" may be any cell known to one skilled in the art, including prokaryotic cells, eukaryotic cells, such as bacterial cells, fungal cells, yeast cells, mammalian cells, insect cells, or plant cells.

To detect the production of an intermediate or product of the methods of the invention, or a new phenotype, at least one metabolic parameter of a cell (or a genetically modified cell) can be monitored in the cell in a "real time" or "on-line" time frame by Metabolic Flux Analysis (MFA). In one aspect, a plurality of cells, such as a cell culture, is monitored in "real time" or "on-line." In one aspect, a plurality of metabolic parameters is monitored in "real time" or "on-line."

Metabolic flux analysis (MFA) is based on a known biochemistry framework. A linearly independent metabolic matrix is constructed based on the law of mass conservation and on the pseudo-steady state hypothesis (PSSH) on the intracellular metabolites. In practicing the methods of the invention, metabolic networks are established, including the:
  identity of all pathway substrates, products and intermediary metabolites
  identity of all the chemical reactions interconverting the pathway metabolites, the stoichiometry of the pathway reactions,
  identity of all the enzymes catalyzing the reactions, the enzyme reaction kinetics,
  the regulatory interactions between pathway components, e.g. allosteric interactions, enzyme-enzyme interactions etc,
  intracellular compartmentalization of enzymes or any other supramolecular organization of the enzymes, and,
  the presence of any concentration gradients of metabolites, enzymes or effector molecules or diffusion barriers to their movement.

Once the metabolic network for a given strain is built, mathematic presentation by matrix notion can be introduced to estimate the intracellular metabolic fluxes if the on-line metabolome data is available. Metabolic phenotype relies on the changes of the whole metabolic network within a cell. Metabolic phenotype relies on the change of pathway utilization with respect to environmental conditions, genetic regulation, developmental state and the genotype, etc. In one aspect of the methods of the invention, after the on-line MFA calculation, the dynamic behavior of the cells, their phenotype and other properties are analyzed by investigating the pathway utilization.

Control of physiological state of cell cultures will become possible after the pathway analysis. The methods of the invention can help determine how to manipulate the fermentation by determining how to change the substrate supply, temperature, use of inducers, etc. to control the physiological state of cells to move along desirable direction. In practicing the methods of the invention, the MFA results can also be compared with transcriptome and proteome data to design experiments and protocols for metabolic engineering or gene shuffling, etc. Any aspect of metabolism or growth can be monitored.

Generating and Manipulating Nucleic Acids

In one aspect, the nitrilase used to practice the methods of the invention is an isolated or a recombinantly generated nitrilase. In one aspect, the nitrilase used to practice the methods of the invention is encoded by a nucleic acid having a sequence at least about 50%, 51%, 52%, 53%, 54%, 55%, 56%, 57%, 58%, 59%, 60%, 61%,62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete identity (100% identical) to SEQ ID NO:1, 3, 5, 7, 9, 11, 13, 15, 17, 19, 21, 23, 25, 27, 29, 31, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 377, 379, 381, 383 and/or 385, or fragments thereof.

In one aspect, the percent identity between two given sequences (nucleic acid or polypeptide) can be calculated using an algorithm such as BLAST (Altschul (1990) J. Mol. Biol. 215:403-410). When using the BLAST algorithm for sequences no longer than 250 nucleotides or about 80 amino acids ("short queries"), the search parameters can be as follows: the filter is off, the scoring matrix is PAM30, the word size is 3 or 2, the E value is 1000 or more, and the gap costs are 11, 1. For sequences longer than 250 nucleotides or 80 amino acid residues, the default search parameters can be used.

Nucleic acids encoding enzymes used to practice the methods of the invention, whether RNA, cDNA, genomic DNA, vectors, viruses or hybrids thereof, may be isolated from a variety of sources, genetically engineered, amplified, and/or expressed/generated recombinantly. Recombinant polypeptides generated from these nucleic acids can be individually isolated or cloned and tested for a desired activity. Any recombinant expression system can be used, including bacterial, mammalian, yeast, insect or plant cell expression systems. Nucleic acids used to practice the methods of the invention, and to make the polynucleotides and polypeptide of the invention, can be generated using amplification methods, which are also well known in the art, and include, e.g., polymerase chain reaction, PCR (see, e.g., PCR PROTOCOLS, A GUIDE TO METHODS AND APPLICATIONS, ed. Innis, Academic Press, N.Y. (1990) and PCR STRATEGIES (1995), ed. Innis, Academic Press, Inc., N.Y., ligase chain reaction (LCR) (see, e.g., Wu (1989) Genomics 4:560; Landegren (1988) Science 241:1077; Barringer (1990) Gene 89:117); transcription amplification (see, e.g., Kwoh (1989) Proc. Natl. Acad. Sci. USA 86:1173); and, self-sustained sequence replication (see, e.g., Guatelli (1990) Proc. Natl. Acad. Sci. USA 87:1874); Q Beta replicase amplification (see, e.g., Smith (1997) J. Clin. Microbiol. 35:1477-1491), automated Q-beta replicase amplification assay (see, e.g., Burg (1996) Mol. Cell. Probes 10:257-271) and other RNA polymerase mediated techniques (e.g., NASBA, Cangene, Mississauga, Ontario).

Alternatively, these nucleic acids can be synthesized in vitro by well-known chemical synthesis techniques, as described in, e.g., Adams (1983) J. Am. Chem. Soc. 105:661; Belousov (1997) Nucleic Acids Res. 25:3440 3444; Frenkel (1995) Free Radic. Biol. Med. 19:373 380; Blommers (1994) Biochemistry 33:7886 7896; Narang (1979) Meth. Enzymol. 68:90; Brown (1979) Meth. Enzymol. 68:109; Beaucage (1981) Tetra. Lett. 22:1859; U.S. Pat. No. 4,458,066.

Techniques for the manipulation of nucleic acids, such as, e.g., subcloning, labeling probes (e.g., random-primer labeling using Klenow polymerase, nick translation, amplification), sequencing, hybridization and the like are well described in the scientific and patent literature, see, e.g., Sambrook, ed., MOLECULAR CLONING: A LABORATORY MANUAL (2ND ED.), Vols. 1-3, Cold Spring Harbor Laboratory, (1989); CURRENT PROTOCOLS IN MOLECULAR BIOLOGY, Ausubel, ed. John Wiley & Sons, Inc., New York (1997); LABORATORY TECHNIQUES IN BIOCHEMISTRY AND MOLECULAR BIOLOGY: HYBRIDIZATION WITH NUCLEIC ACID PROBES, Part I. Theory and Nucleic Acid Preparation, Tijssen, ed. Elsevier, N.Y. (1993). Another useful means of obtaining and manipulating nucleic acids used to practice the methods of the invention is to clone from genomic samples, and, if desired, screen and re-clone inserts isolated or amplified from, e.g., genomic clones or cDNA clones. Sources of nucleic acid used in the methods of the invention include genomic or cDNA libraries contained in, e.g., mammalian artificial chromosomes (MACs), see, e.g., U.S. Pat. Nos. 5,721,118; 6,025,155; human artificial chromosomes, see, e.g., Rosenfeld (1997) Nat. Genet. 15:333-335; yeast artificial chromosomes (YAC); bacterial artificial chromosomes (BAC); P1 artificial chromosomes, see, e.g., Woon (1998) Genomics 50:306-316; P1-derived vectors (PACs), see, e.g., Kern (1997) Biotechniques 23:120-124; cosmids, recombinant viruses, phages or plasmids.

Another useful means of obtaining and manipulating nucleic acids used to practice the methods of the invention is to clone from genomic samples, and, if desired, screen and re-clone inserts isolated or amplified from, e.g., genomic clones or cDNA clones. Sources of nucleic acid used in the methods of the invention include genomic or cDNA libraries contained in, e.g., mammalian artificial chromosomes (MACs), see, e.g., U.S. Pat. Nos. 5,721,118; 6,025,155; human artificial chromosomes, see, e.g., Rosenfeld (1997) Nat. Genet. 15:333-335; yeast artificial chromosomes (YAC); bacterial artificial chromosomes (BAC); P1 artificial chromosomes, see, e.g., Woon (1998) Genomics 50:306-316; P1-derived vectors (PACs), see, e.g., Kern (1997) Biotechniques 23:120-124; cosmids, recombinant viruses, phages or plasmids.

The invention will be further described with reference to the following examples; however, it is to be understood that the invention is not limited to such examples.

EXAMPLES

Example 1

Materials: 3-hydroxyglutaronitrile was purchased from TCI America. (R)-3-hydroxy-4-cyanobutyric acid was obtained from Gateway Chemical Technology (St. Louis, Mo.). All other reagents were purchased from Sigma Aldrich and utilized without further purification. Silica Gel, 70-230 mesh, 60 Å, purchased from Aldrich, was used for chromatographic purifications.

I. (a) Preparation of 3-hydroxy-glutaronitrile (HGN)

KCN (1.13 mol, 61.7 g) was dissolved in water (160 ml) at 20° C. The pH of the solution was adjusted to and maintained at pH 10.0 by addition of 6 M HCl acid via an automated burette and below 10° C. by cooling in an ice bath. Epichlorohydrin (0.60 mol, 55.5 g) was added dropwise while the temperature was maintained below 10° C. The reaction was allowed to proceed at 10° C. until the pH of the solution begins to drop below 10. At this point the pH was maintained at 10.0 by the addition on 6N KOH via pH stat and the reaction was allowed to proceed overnight with stirring at 20° C. The solution was then adjusted to pH7 by addition of 6 N HCl and then continuously extracted with EtOAc (400 ml) for 48 h. The organic extract was dried over $Na_2SO_4$ and then concentrated in vacuo. Crude 3-glutaronitrile was obtained in 85% yield as a deep red liquid (57 g, 0.52 mol). The product was purified by vacuum distillation to obtain hydroxyglutarol nitrile as a clear yellow liquid in 59% yield (0.35 mol, 39 g) $^1$H NMR ($D_2O$): 4.40 (m, 1H), 2.89 (m, 4H). $^{13}$C NMR ($D_2O$): 117.3, 61.91, 23.69. MS calc'd for [$C_5H_6N_2O$]: 110.05, found: 110.00 [M$^+$], (ESI+).

II. a) Hydrolysis of 3-hydroxy-glutaronitrile (Purified) With Nitrilase 3-hydroxyglutaronitrile (1 g, 9 mmol) was suspended in 37.5 mL of $N_2$ (g) sparged, room temperature, 100 mM sodium phosphate buffer at pH 7. To this 240 mM solution of HGN was added 150 mg of cell lysate normalized for protein content. As assessed by PAGE, the nitrilase content was established to be 20% of the total protein. Therefore effectively, 30 mg of nitrilase is used in this reaction. The reaction was agitated at 100 rpm. Reaction progress was monitored by TLC (1:1 EtOAc:Hexanes, $R_f$=0.32, nitrile; $R_f$=0.0, acid) and GC. After 22 h, the reaction was filtered through a 10,000 MW cutoff filter and then concentrated in vacuo. The concentrated hydrolysis solution was acidified with 1M HCl and the product was continuously extracted with MTBE (30 mL). The acid product (R)-3-hydroxy-4-cyanobutyric acid was isolated as a yellow oil (1.15 g, 98% yield). $^1$H NMR ($d_6$-DMSO, 500 MHz) δ12.32 (s, 1H), 5.52 (s, 1H), 4.10 (m, 1H), 2.70 (dd, 1H, J=16.8, 4.1 Hz), 2.61 (dd, 1H, J=16.9, 6.3 Hz), 2.44 (dd, 1H, J=15.4, 5.3 Hz), 2.37 (dd, 1H, J=15.6, 7.8 Hz). $^{13}$C NMR (DMSO, 298K, 125 MHz) δ171.9, 118.7, 63.4, 41.2, 25.2 MS calc'd for [$C_5H_7NO_3$]: 129.0, found: 130.0 [M+H$^+$], (ESI+). ee=95% [HPLC]. Based on the isolated yield a productivity of 40 g g$^{-1}$ d$^{-1}$ is calculated.

b) Integrated Process for Preparation of HGN, Hydrolysis of 3-hydroxy-glutaronitrile (Crude) with Nitrilase, Ca(OH)$_2$ Precipitation and Esterification KCN (1.13 mol, 61.7 g) was dissolved in water (160 ml) at 20° C. The pH of the solution was adjusted to and maintained at pH 10.0 by addition of 6 M HCL acid via an automated burette and below 10° C. by cooling in an ice bath. Epichlorohydrin (0.60 mol, 55.5 g) was added dropwise while the temperature was maintained below 10° C. The reaction was allowed to proceed at 10° C. until the pH of the solution begins to drop below 10. At this point the pH was maintained at 10.0 by the addition on 6N KOH via pH stat and the reaction was allowed to proceed overnight with stirring at 20° C. The solution was then adjusted to pH7 by addition of 6 N HCl. The final concentration of HGN in this reaction was assessed to be 1.24 M A portion of this crude solution of HGN (7.4 mL) was diluted with 33.6 mL pH 7 100 mM phosphate. To this solution was added 100 mg of cell lysate, normalized for protein content, which had been suspended in 5 mL 100 mM phosphate buffer. The reaction mixture contained 9.25 mmol HGN in 46 mL buffer at a final concentration of 200 mM As assessed by PAGE, the nitrilase content was established to be 20% of the total protein. Therefore effectively, 20 mg of nitrilase is used in this reaction. The reaction was agitated at room temperature at 100 rpm. Reaction progress was monitored by TLC (1:1 EtOAc:Hexanes, $R_f$=0.32, nitrile; $R_f$=0.0, acid) After all the HGN was consumed (22 hours), the reaction solution was filtered through celite.

The filtered solution was cooled in an ice-water bath and then 3 g calcium hydroxide monohydrate was added to it. Ethanol (85 mL) was added to the above suspension and after stirring for 1 hour the resulting white solid was filtered, washed with ethanol and dried in vacuo overnight. The calcium salt was isolated as a white solid (4.6 g). This material was suspended in 50 ml of 200 proof ethanol, cooled by an ice-water-salt bath, and then 1 ml concentrated sulfuric acid was added dropwise. Once acidified the solution was subjected to reflux for one hour. After cooling the solid impurities were removed by filtration and the filtrate was concentrated in vacuo. Pure (R)-ethyl 4-cyano-3-hydroxybutyrate (1.1 g, 79% yield based on epichlorohydrin, 93% ee) was isolated as a pale yellow oil by Kugelrohr distillation.

(c) Crystallization of Potassium 4-cyano-3-hydroxybutyrate

Method one: To a 1 g of 4-cyano-3-hydroxybutyric acid in 10 mL water, chilled on an ice bath, was added a concentrated solution of KOH (20% w/v, 1.05 equivalents). This solution was concentrated to dryness in vacuo and then the residue was recrystallized from hot ethanol. White needle crystals were formed and resulted in an enantiomeric excess enhancement from 93% ee to 97% ee with up to 80% recovery achieved to date. This was performed several times on one gram scale and once at a 10 g scale.

Method Two: To a 1 g of 4-cyano-3-hydroxybutyric acid in 15 mL methanol was added a concentrated methanolic solution of KOH (20% w/v, 1.05 equivalents). To this solution was added MTBE to initiate crystallization. This procedure yielded an enantiomeric excess enhancement from 94% ee to 98% ee with 88% yield achieved to date. A second recrystallization afforded an enrichment from 98% ee to 99.6% ee (80% yield). In addition, in a single crystallization 95.5% ee samples were enriched to 99.2% (20% yield on first attempt). The crystallization methods have not been optimized. This was performed several times on a one gram scale.

III (a) Synthesis of (R)-Ethyl 4-cyano-3-hydroxybutyric With HCl Catalyst

A 0.2 M solution of (R)-3-hydroxy-4-cyanobutyric acid (50 mg, 0.4 mmol) in anhydrous ethanol (1.94 mL) was prepared. The ethanol solution was added dropwise to 1.0 ml of a 50:50 (v/v) mixture of anhydrous 1 M HCl ethereal solution and anhydrous ethanol over molecular sieves. The reaction was stirred overnight at room temperature under $N_2$. The reaction was monitored by TLC, (1:1 EtOAc:Hexanes, $R_f$=0.45, ester; $R_f$=0.0, acid, stained with p-anisaldehyde). After 30 h, solvent was removed in vacuo. The crude product was taken up in $Et_2O$ (25 mL), washed with 5 ml saturated bicarbonate and then 5 mL brine. The organic extract was dried over $MgSO_4$, filtered and then concentrated in vacuo, yielding the product as a clear oil. $^1H$ NMR (DMSO, 298K, 500 MHz) δ5.60 (d, 1H, J=5.58 Hz), 4.12 (m, 1H), 4.07 (q, 2H, J=7.1), 2.66 (m, 2H), 2.47 (m, 2H), 1.87 (t, 3H, J=7.0). $^{13}C$ NMR (DMSO, 298K, 125 MHz) δ170.21, 118.60, 63.40, 59.98, 41.10, 25.14, 14.02. MS calc'd for $[C_7H_{11}NO_3]$: 157.1, found 158.2. [M+H$^+$]

(b) Synthesis of (±)-Ethyl 4-cyano-3-hydroxybutyrate With $H_2SO_4$ Catalyst A 1 M solution of 4-cyano-3-hydroxybutyric acid in anhydrous ethanol was prepared and cooled in an ice bath. Several drops of concentrated sulfuric acid was added. The reaction mixture was then subjected to reflux for 4 hours to overnight. After reaction, the solvent was removed in vacuo. Ethyl ester formation was found to be quantitative.

Analytical Information

All $^1H$ and $^{13}C$ NMR spectra were run on Bruker model AM-500 instruments, set at room temperature, 500 MHz and 125 MHz respectively for $^1H$ and $^{13}C$. GC analysis was performed on an Agilent 6890 GC with a Macherey-Nagel Lipodex A column, using a FID detector. The HPLC analysis was performed on an Agilent 1100 HPLC with a Daicel OD column (50×0.46 cm) and the DAD detector set at 210, 220, and 250 nm. Specific rotation was determined on a Perkin Elmer Model 341 Polarimeter, set at 589 nm, Na lamp, at room temperature, with a 100 mm path length cell. Concentrations (c) for specific rotation are reported in grams per 100 ml of solvent.

| | Analytical Methods: | | | |
|---|---|---|---|---|
| | Acid Product | Column | Chromatography Method Details | Retention Times Of enantiomers (min) |
| HPLC | 4-cyano-3-hydroxybutyrate | Daicel OD 50 × 4.6 mm | 5% isopropanol, 95% hexane 1 ml/min | 4.5 (R); 5.4 (S) |
| GC | Methyl 4-cyano-3-hydroxybutyrate | Lipodex A 25 m Macherey-Nagel | 95° C., 1 ml/min | 51.6 (R); 52.7 (S) |

Preparation of (R)-(−)-Methyl 4-cyano-3-hydroxybutyrate (R)-4-cyano-3-hydroxybutyric acid (658 mg, 5.1 mmol) was dissolved in methanol (20 ml) and the solution was treated with dropwise addition of TMS-diazomethane (2 M solution in hexane, 150 mmol) at 22° C. for 1 hr to yield the methyl ester product. The mixture was concentrated in vacuo, extracted with ethyl acetate (3×40 ml) and then the combined organic extracts were dried over $MgSO_4$, filtered and concentrated in vacuo giving a yellow oil (549 mg, 3.84 mmol, 74% yield). $^1H$ NMR (DMSO, 298K, 500 MHz) δ5.60 (d, 1H, J=5.26 Hz), 4.13 (m, 1H), 3.60 (s 3H), 2.71 (dd, 1H, J=16.9, 4.2 Hz,), 2.63 (dd, 1H, J=16.9, 6.7), 2.54 (dd, 1H, J=14.9, 4.9), 2.44 (dd, 1H, J=15.7, 7.9) $^{13}C$ NMR (DMSO, 298K, 125 MHz) 170.7, 118.6, 63.4, 51.4, 40.9, 25.1, Exact Mass Calculated for $[C_6H_9NO_3]$: 143.1, found: 144.0 [M+H$^+$].

Benzoyl chloride (0.068 ml, 0.75 mmol) was added to a stirred solution of (R)-methyl 4-cyano-3-hydroxybutyrate (72 mg, 0.5 mmol) in pyridine (2 ml), at room temperature. After 19 hours, an additional 0.5 equivalent of benzoyl chloride (0.023 ml, 0.25 mmol) was added. After 24 h, 1 ml water was added to the reaction mixture that was then extracted with diethyl ether (3×10 ml). The combined organic extracts were washed with brine (2×10 ml), dried over $MgSO_4$, filtered and concentrated in vacuo. The crude product was purified by silica gel flash chromatography (eluant hexane:ethyl acetate [2:1]) yielding a yellow oil (46 mg, 0.19 mmol, 37%). $^1H$ NMR (DMSO, 298K, 500 MHz) d 7.96 (d, 2H, J=7.8), 7.70 (t, 1H, J=7.25), 7.56 (t, 2H, J=7.8), 5.55 (m, 1H), 3.59 (s, 3H), 3.13 (m, 2H), 2.90 (m, 2H). $^{13}C$ NMR (DMSO, 298K, 125 MHz) d 169.6, 164.5, 133.8, 129.3, 128.9, 128.5, 117.3, 66.0, 51.8, 37.5, 22.2 MS calc'd for $[C_{13}H_{13}NO_4]$: 247.25, found: 270.3 [M+Na$^+$] ee=95% [HPLC]. $[\alpha]^{20}_{598}$ −32.4 (c=0.5, CHCl$_3$).

Example 2

The following is an exemplary protocol for making (R)-ethyl 4-cyano-3-hydroxybutyric acid by a "one pot process" and a "multi-pot" process. Other exemplary variations to the methods of the invention are also described, including those that can be practiced in processes of the invention other than the exemplary "one pot" or a "multipot" process described herein.

1) This method includes the sequential preparation of HGN (3-hydroxyglutaronitrile) from epichlorohydrin followed by the addition of neutralizing agent, buffer or other diluents and then subsequent transformation with a nitrilase or the direct addition of a nitrilase to the crude reaction of the HGN production. In addition, an ester of 4-cyano-3-hydroxy butyrate may be made in the same pot through a variety of methods (see step 5, below).

Sequential pots can also be used where the crude of purified materials are transferred to new vessels.

2) In one aspect, the process is carried out with and/or without the crystallization step or with and without the Ca salt precipitation step.

3) In one aspect, the nitrilase reaction is applied to purify crude HGN.

Purification can be by distillation, column chromatography, crystallization (e.g. K+ salt) or precipitation (e.g. CaCl2), or any method known in the art.

4) Various types of crystallizing salts (not only potassium) can be used. Other types of crystallizing salts can be used include sodium, lithium, rubidium, cesium or any other monovalent or divalent metal.

5) The invention provides several ways of performing esterification, include Fisher esterification, catalyzed by HCl, sulfuric acid, or other acids including acidic resins.

The invention also provides for preparation of tert-butyl esters by treatment with tert-butyl ethers of the salt with tert-butyl bromide and the preparation of esters by treatment of carboxylic acid with dehydrating agents (e.g. DCC-dicyclohexylcarbodimide) and an alcohol. The methods of the invention can be practiced with any protocol for the preparation of esters, including Mitsunobu conditions or any other method known in the art, including trans-esterification.

6) The methods of the invention can be practiced with other esters if possible: Methyl, ethyl, propyl, iso-propyl, butyl etc.

7) Process can be performed in directly in a fermentor with cell, with whole cell paste (e.g., wet or dry, immobilized or free), using cell lysates (e.g., crude or clarified, lyophilized or not, immobilized or free).

The methods of the invention can be practiced with purified or partially purified nitrilase. Nitrilase (cells etc) can be encapsulated within a gel.

8) The process of the invention can be run in a batch wise process or via pulsed or continuous feeding of substrate in a number of reactor configurations, including a membrane reactor or column.

9) The process of the invention can be run using temperatures in the range of 1° C., 2° C., 4° C., 10° C., 20° C., 22° C., 30° C., 37° C., 40° C., 50° C., 60° C., 70° C., 80° C., 90° C., 95° C., 99° C. (i.e. anywhere in the range of between about 1°-99° C.).

10) The process of the invention can be run using pH in the range of about 5 to about 9, or, from about pH 4 to about pH 11.

11) The process of the invention can be run using substrate concentrations as high at 5 M and as low as 10 mM.

12) The process of the invention can be run using various ionic strengths and buffer conditions. The process of the invention can be run using no buffer under pH stat conditions or in unbuffered saline.

A number of embodiments of the invention have been described. Nevertheless, it will be understood that various modifications may be made without departing from the spirit and scope of the invention. Accordingly, other embodiments are within the scope of the following claims.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US07932064B2). An electronic copy of the "Sequence Listing" will also be available from the USPTO upon request and payment of the fee set forth in 37 CFR 1.19(b)(3).

What is claimed is:

1. A method for making (R)-ethyl-4-cyano-3-hydroxybutyrate, comprising
   (a) providing an epichlorohydrin;
   (b) providing a polypeptide having an amino acid sequence with at least 80% sequence identity to SEQ ID NO:210 and having nitrilase activity
   (c) preparing a 3-hydroxyglutaronitrile (HGN) from the epichlorohydrin, followed by the addition of a neutralizing agent, a buffer or a diluent,
   wherein the epichlorohydrin is converted to 3-hydroxyglutaronitrile (HGN) by cyanide treatment;
   (d) catalyzing the conversion of the 3-hydroxyglutaronitrile (HGN) to 4-cyano-3-hydroxybutyric acid by contacting the 3-hydroxyglutaronitrile (HGN) with the polypeptide of step (b);
   (e) isolating the 4-cyano-3-hydroxybutyric acid made in step (d) by crystallization using a protocol comprising:
      (1) adding concentrated potassium hydroxide or calcium hydroxide to the 4-cyano-3-hydroxybutyric acid, followed by concentration of the solution and crystallization precipitation using a hot alcohol, or
      (2) converting the 4-cyano-3-hydroxybutyric acid to its potassium salt by reaction with potassium hydroxide in water or an alcohol, followed by crystallization of the 4-cyano-3-hydroxybutyric acid potassium salt; or
      (3) the protocol of (e)(1) or (e)(2) further comprising a second or additional recrystallization after re-suspension of the crystals formed in (e)(1) or (e)(2); and
   (f) converting the crystallization precipitate to (R)-Ethyl-4-Cyano-3-Hydroxybutyrate by esterification using an acid catalyst.

2. The method of claim 1, wherein the polypeptide of step (b) is an isolated, synthetic, or recombinant nitrilase.

3. The method of claim 1, wherein the acid catalyst esterification of the (R)-Ethyl-4-Cyano-3-Hydroxybutyrate comprises use of a hydrochloric acid (HCl) catalyst or a sulfuric acid ($H_2SO_4$) catalyst.

4. The method of claim 1, wherein the reaction is a one-pot reaction.

5. The method of claim 1, wherein at least two steps of the reaction take place in sequential pots.

6. The method of claim 1, wherein the preparing of the 3-hydroxyglutaronitrile (HGN) from the epichlorohydrin comprises adding the epichlorohydrin to an aqueous solution of potassium cyanide (KCN) at an alkaline pH.

7. The method of claim 1, wherein hydroxyglutaronitrile (HGN) is converted to 4-cyano-3-hydroxybutyric acid with the polypeptide of step (b) under conditions comprising:
(a) adding to an HGN-comprising pH neutral phosphate buffered solution a cell lysate comprising a recombinantly expressed polypeptide having nitrilase activity, wherein the polypeptide catalyzes the hydrolysis of the HGN to produce 4-cyano-3-hydroxybutyric acid; or,
(b) the method of (a), wherein the 4-cyano-3-hydroxybutyric acid-comprising hydrolysis solution is acidified and the 4-cyano-3-hydroxybutyric acid extracted and isolated as an oil.

8. The method of claim 1, wherein the polypeptide of step (b) comprises the sequence as set forth in SEQ ID NO:210 and having a mutation at residue 190 from alanine to a histidine residue.

9. The method of claim 1, wherein the polypeptide of step (b) comprises the sequence as set forth in SEQ ID NO:210 having a mutation at residue 190, wherein alanine at position 190 is replaced with an amino acid capable of receiving or donating a hydrogen bond.

10. The method of claim 1, wherein the polypeptide of step (b) comprises the sequence as set forth in SEQ ID NO: 210 and having a mutation at residue 190, wherein alanine at position 190 is replaced with a hydrophobic amino acid.

11. The method of claim 1, wherein the polypeptide of step (b) comprises the sequence as set forth in SEQ ID NO:210 and having one or more mutations at amino acid residue 55 from alanine to a lysine, glycine, or glutamine; at amino acid residue 60 from isoleucine to a glutamic acid; at amino acid residue 111 from asparagine to a serine, at amino acid residue 190 from alanine to a serine, histidine, tyrosine or threonine; at amino acid residue 191 from phenylalanine to a leucine, valine, methionine, aspartic acid, glycine, glutamic acid, tyrosine or threonine; at amino acid residue 199 from methionine to a glutamic acid or leucine; or at amino acid residue 222 from aspartic acid to a leucine.

12. The method of claim 1, wherein the polypeptide having nitrilase activity is encoded by a nucleic acid having a sequence with at least 95% sequence identity to SEQ ID NO:209.

13. The method of claim 1, wherein the nitrilase polypeptide has a sequence with at least 90% sequence identity to SEQ ID NO:210.

14. The method of claim 13, wherein the nitrilase polypeptide has a sequence with at least 95% sequence identity to SEQ ID NO:210.

15. The method of claim 14, wherein the nitrilase polypeptide has a sequence with at least 98% sequence identity to SEQ ID NO:210.

16. A method for making (R)-ethyl-4-cyano-3-hydroxybutyrate comprising
(A) (a) providing an epichlorohydrin;
(b) providing a polypeptide having an amino acid sequence with at least 80% identity to SEQ ID NO:210 and having nitrilase activity;
(c) preparing a 3-hydroxyglutaronitrile (HGN) from the epichlorohydrin, followed by the addition of a neutralizing agent, a buffer or a diluent,
wherein the epichlorohydrin is converted to 3-hydroxyglutaronitrile (HGN) by cyanide treatment under pH and temperature control, and the conversion process comprises adding the epichlorohydrin to an aqueous solution of potassium cyanide (KCN) at an alkaline pH;
(d) without any purification of the HGN made in step (c), catalyzing the conversion of the 3-hydroxyglutaronitrile (HGN) to 4-cyano-3-hydroxybutyric acid by contacting the 3-hydroxyglutaronitrile (HGN) with the polypeptide of step (b) under conditions comprising:
(1) adding to an HGN-comprising pH neutral phosphate buffered solution a cell lysate comprising a recombinantly expressed polypeptide of step (b), wherein the polypeptide catalyzes the hydrolysis of the HGN to produce 4-cyano-3-hydroxybutyric acid; or,
(2) the method of (a), wherein the 4-cyano-3-hydroxybutyric acid-comprising hydrolysis solution is acidified and the 4-cyano-3-hydroxybutyric acid extracted and isolated as an oil;
(e) isolating the 4-cyano-3-hydroxybutyric acid made in step (d) by crystallization using a protocol comprising:
(1) adding concentrated potassium hydroxide or calcium hydroxide to the 4-cyano-3-hydroxybutyric acid, followed by concentration of the solution and crystallization precipitation using hot ethanol, or
(2) converting the 4-cyano-3-hydroxybutyric acid to its potassium salt by reaction with potassium hydroxide in water, methanol or ethanol, followed by crystallization of the 4-cyano-3-hydroxybutyric acid potassium salt; or
(3) a second or additional recrystallization after re-suspension of the crystals formed in (e)(1) or (e)(2); and
(f) converting the crystallization precipitate to (R)-Ethyl-4-Cyano-3-Hydroxybutyrate by esterification using an acid catalyst,
wherein the acid catalyst esterification of the (R)-Ethyl-4-Cyano-3-Hydroxybutyrate comprises use of a hydrochloric acid (HCl) catalyst or a sulfuric acid ($H_2SO_4$) catalyst.

17. The method of claim 16, wherein the reaction is a one-pot reaction.

18. The method of claim 16, wherein at least two steps of the reaction take place in sequential pots.

19. The method of claim 16, further comprising converting the 4-cyano-3-hydroxybutyric acid to its potassium salt by reaction with a potassium hydroxide in water, methanol or ethanol.

20. The method of claim 15, wherein the nitrilase polypeptide has a sequence that has 100% sequence identity to SEQ ID NO:210, or has a sequence as set forth in SEQ ID NO:210 with a residue change comprising A190H.

21. The method of claim 16, wherein the recombinant nitrilase polypeptide is encoded by a nucleic acid having a sequence with at least 90% sequence identity to SEQ ID NO:209.

22. The method of claim 21, wherein the recombinant nitrilase polypeptide is encoded by a nucleic acid having a sequence with at least 95% sequence identity to SEQ ID NO:209.

23. The method of claim 22, wherein the recombinant nitrilase polypeptide is encoded by a nucleic acid having a sequence with at least 98% sequence identity to SEQ ID NO:209.

24. The method of claim 23, wherein the recombinant nitrilase polypeptide is encoded by a nucleic acid having a sequence with at least 99% sequence identity to SEQ ID NO:209.

25. The method of claim 24, wherein the recombinant nitrilase polypeptide is encoded by a nucleic acid having 100% sequence identity to SEQ ID NO:209, or has a sequence as set forth in SEQ ID NO:209 but encoding a polypeptide with an amino acid residue change A190H.

26. The method of claim 16, wherein the recombinant nitrilase polypeptide has a sequence with at least 90% sequence identity to SEQ ID NO:210.

27. The method of claim 1, wherein the alcohol comprises a methanol or an ethanol.

28. The method of claim 1, wherein the 4-cyano-3-hydroxybutyric acid generated in step (d) has a chiral purity of at least 90% ee.

29. A method for making 4-cyano-3-hydroxybutyric acid comprising
(A) (a) providing an epichlorohydrin;
(b) providing a polypeptide having an amino acid sequence with at least 80% identity to SEQ ID NO:210 and having nitrilase activity;
(c) preparing a 3-hydroxyglutaronitrile (HGN) from the epichlorohydrin, followed by the addition of a neutralizing agent, a buffer or a diluent,
wherein the epichlorohydrin is converted to 3-hydroxyglutaronitrile (HGN) by cyanide treatment under pH and temperature control, and the conversion process comprises adding the epichlorohydrin to an aqueous solution of potassium cyanide (KCN) at an alkaline pH;
(d) without any purification of the HGN made in step (c), catalyzing the conversion of the 3-hydroxyglutaronitrile (HGN) to 4-cyano-3-hydroxybutyric acid by contacting the 3-hydroxyglutaronitrile (HGN) with the polypeptide of step (b) under conditions comprising:
(1) adding to an HGN-comprising pH neutral phosphate buffered solution a cell lysate comprising a recombinantly expressed polypeptide having nitrilase activity, wherein the polypeptide catalyzes the hydrolysis of the HGN to produce 4-cyano-3-hydroxybutyric acid; or,
(2) the method of (a), wherein the 4-cyano-3-hydroxybutyric acid-comprising hydrolysis solution is acidified and the 4-cyano-3-hydroxybutyric acid extracted and isolated as an oil.

30. The method of claim 29, further comprising isolating the 4-cyano-3-hydroxybutyric acid made in step (d) by crystallization using a protocol comprising:
(1) adding concentrated potassium hydroxide or calcium hydroxide to the 4-cyano-3-hydroxybutyric acid, followed by concentration of the solution and crystallization precipitation using hot ethanol, or
(2) converting the 4-cyano-3-hydroxybutyric acid to its potassium salt by reaction with potassium hydroxide in water, methanol or ethanol, followed by crystallization of the 4-cyano-3-hydroxybutyric acid potassium salt; or
(3) a second or additional recrystallization after re-suspension of the crystals formed in (e)(1) or (e)(2).

31. The method of claim 30, further comprising converting the crystallization precipitate to an ethyl-4-cyano-3-hydroxybutyrate by esterification using an acid catalyst.

32. The method of claim 31, wherein the acid catalyst esterification of the ethyl-4-cyano-3-hydroxybutyrate comprises use of a hydrochloric acid (HCl) catalyst or a sulfuric acid ($H_2SO_4$) catalyst.

* * * * *